United States Patent
Tsuboyama et al.

(10) Patent No.: US 6,780,528 B2
(45) Date of Patent: Aug. 24, 2004

(54) LUMINESCENCE DEVICE AND METAL COORDINATION COMPOUND THEREFOR

(75) Inventors: Akira Tsuboyama, Sagamihara (JP); Hidemasa Mizutani, Sagamihara (JP); Shinjiro Okada, Isehara (JP); Takao Takiguchi, Tokyo (JP); Takashi Moriyama, Kawasaki (JP); Jun Kamatani, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/961,150

(22) Filed: Sep. 24, 2001

(65) Prior Publication Data

US 2002/0068190 A1 Jun. 6, 2002

(30) Foreign Application Priority Data

Sep. 26, 2000 (JP) ........................................ 2000/292491
Sep. 19, 2001 (JP) ........................................ 2001/284601

(51) Int. Cl.$^7$ .............................................. H05B 33/14
(52) U.S. Cl. ........................ 428/690; 428/917; 313/504; 313/506; 257/102; 257/103
(58) Field of Search ................................. 428/690, 704, 428/917; 313/504, 506; 252/301.16; 257/102, 103; 544/225; 546/2; 548/101, 402

(56) References Cited

U.S. PATENT DOCUMENTS

| | | | |
|---|---|---|---|
| 5,698,858 A | 12/1997 | Börner | 250/484.2 |
| 6,097,147 A | 8/2000 | Baldo et al. | 313/506 |
| 2002/0034656 A1 * | 3/2002 | Thompson et al. | 428/690 |

FOREIGN PATENT DOCUMENTS

| | | |
|---|---|---|
| JP | 8-319482 | 12/1996 |
| JP | 11-256148 | 9/1999 |
| JP | 11-329739 | 11/1999 |
| WO | WO 00/57676 | 9/2000 |

OTHER PUBLICATIONS

M. Maestri et al., "Photochemistry and Luminescence of Cyclometallated Complexes", Advances in Photochemistry, vol. 17, 1992, pp. 1–68.*
European Search Report in Application No. 01122939.0 (May 7, 2003).
C.H. Chen et al., "Recent Developments in Molecular Organic Electroluminescent Materials," 125 *Macromol. Symp.* 1–48 (1997).
D.F. O'Brien et al., "Improved Energy Transfer in Electrophosphorescent Devices," 74(3) *Appl. Phys. Lett.* 442–444 (Jan. 1999).
M.A. Baldo et al., "Very High–Efficiency Green Organic Light–Emitting Devices Based on Electrophosphorescense," 75(1) *Appl. Phys. Lett.* 4–6 (Jul. 1999).

* cited by examiner

*Primary Examiner*—Marie Yamnitzky
(74) *Attorney, Agent, or Firm*—Fitzpatrick, Cella, Harper & Scinto

(57) ABSTRACT

A luminescence device is principally constituted by a pair of electrodes and an organic compound layer disposed therebetween. The organic compound layer contains a metal coordination compound characterized by having a partial structure represented by the following formula (1):

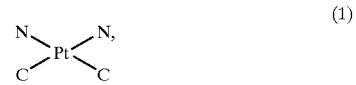

wherein each of N and C represents an atom constituting a cyclic group.

1 Claim, 1 Drawing Sheet

LUMINESCENCE DEVICE AND METAL COORDINATION COMPOUND THEREFOR

FIELD OF THE INVENTION AND RELATED ART

The present invention relates to a luminescence device and a metal coordination compound therefor. More specifically, the present invention relates to a luminescence device employing an organic metal coordination compound having a platinum center metal as a luminescence material so as to allow stable luminescence efficiency, and a metal coordination compound adapted for use in the luminescence device.

An organic electroluminescence EL device has been extensively studied as a luminescence device with a high responsiveness and high efficiency.

The organic EL device generally has a sectional structure as shown in FIG. 1A or 1B (e.g., as described in "Macromol. Symp.", 125, pp. 1–48 (1997)).

Referring to the figures, the EL device generally has a structure including a transparent substrate 15, a transparent electrode 14 disposed on the transparent substrate 15, a metal electrode 11 disposed opposite to the transparent electrode 14, and a plurality of organic (compound) layers disposed between the transparent electrode 14 and the metal electrode 11.

Referring to FIG. 1, the EL device in this embodiment has two organic layers including a luminescence layer 12 and a hole transport layer 13.

The transparent electrode 14 may be formed of a film of ITO (indium tin oxide) having a larger work function to ensure a good hole injection performance into the hole transport layer. On the other hand, the metal electrode 11 may be formed of a layer of aluminum, magnesium, alloys thereof, etc., having a smaller work function to ensure a good electron injection performance into the organic layer(s).

These (transparent and metal) electrodes 14 and 11 may be formed in a thickness of 50–200 nm.

The luminescence layer 12 may be formed of, e.g., an aluminum quinolinol complex (representative example thereof may include Alq3 described hereinafter) having an electron transporting characteristic and a luminescent characteristic. The hole transport layer 13 may be formed of, e.g., a triphenyldiamine derivative (representative example thereof may include α-NPD described hereinafter) having an electron donating characteristic.

The above-described EL device exhibits a rectification characteristic, so that when an electric field is applied between the metal electrode 11 as a cathode and the transparent electrode 14 as an anode, electrons are injected from the metal electrode 11 into the luminescence layer 12 and holes are injected from the transparent electrodes 14.

The thus-injected holes and electrons are recombined within the luminescence layer 12 to produce excitons, thus causing luminescence. At that time, the hole transport layer 13 functions as an electron-blocking layer to increase a recombination efficiency at the boundary between the luminescence layer 12 and the hole transport layer 13, thus enhancing a luminescence efficiency.

Referring to FIG. 1B, in addition to the layers shown in FIG. 1A, an electron transport layer 16 is disposed between the metal electrode 11 and the luminescence layer 12, whereby an effective carrier blocking performance can be ensured by separating the functions of luminescence, electron transport and hole transport, thus allowing effective luminescence.

The electron transport layer 16 may be formed of, e.g., oxadiazole derivatives.

In ordinary organic EL devices, fluorescence caused during a transition of a luminescent center molecule from a singlet excited state to a ground state is used as luminescence.

On the other hand, not the above fluorescence (luminescence) via singlet exciton, but phosphorescence (luminescence) via a triplet exciton has been studied for use in an organic EL device as described in, e.g., "Improved energy transfer in electrophosphorescent device" (D. F. O'Brien et al., Applied Physics Letters, Vol. 74, No. 3, pp. 442–444 (1999)) and "Very high-efficiency green organic light-emitting devices based on electrophosphorescence" (M. A. Baldo et al., Applied Physics Letters, Vol. 75, No. 1, pp. 4–6(1999)).

The EL devices shown in these documents may generally have a sectional structure shown in FIG. 1C.

Referring to FIG. 1C, four organic layers including a hole transfer layer 13, a luminescence layer 12, an exciton diffusion-prevention layer 17, and an electron transport layer 16 are successively formed in this order on the transparent electrode (anode) 14.

In the above documents, higher efficiencies have been achieved by using four organic layers including a hole transport layer 13 of α-NPD (shown below), an electron transport layer 16 of Alq3 (shown below), an exciton diffusion-prevention layer 17 of BPC (shown below), and a luminescence layer 12 of a mixture of CPB (shown below) as a host material with Ir(ppy)₃ (shown below) or PtOEP (shown below) as a guest phosphorescence material doped into CBP at a concentration of ca. 6 wt. %.

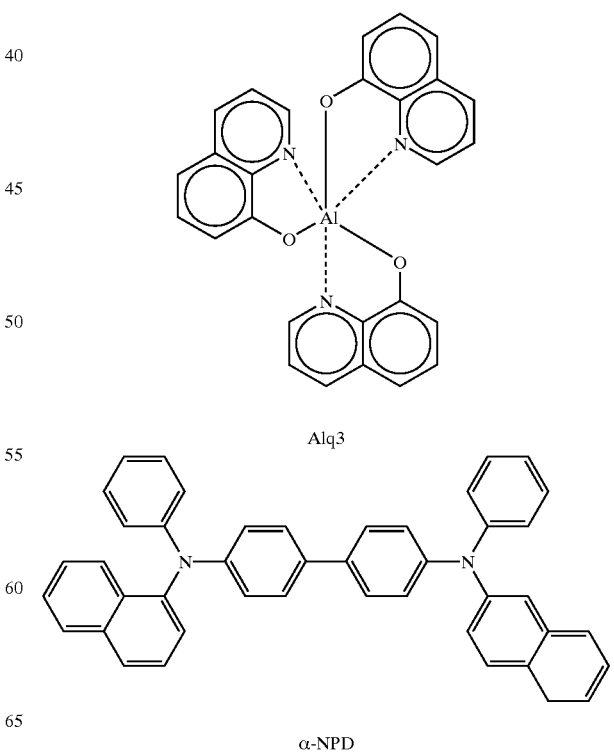

Alq3

α-NPD

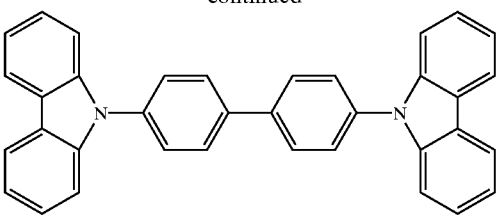

CBP

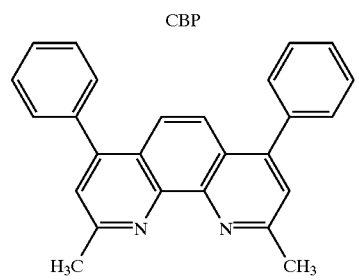

BCP

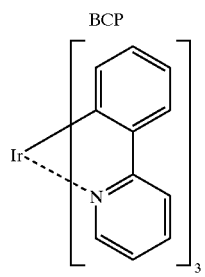

Ir(ppy)₃

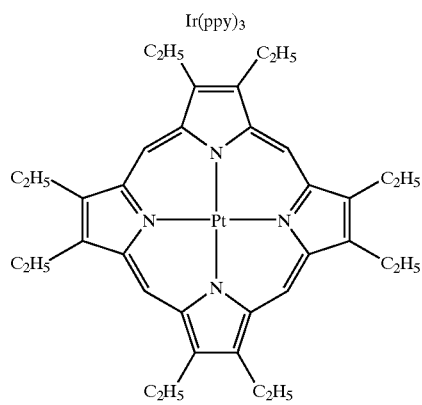

pt-OEP

Alq3: tris(8-hydroxyquinoline) aluminum (aluminum-quinolinol complex),

α-NPD: N4,N4'-di-naphthalene-1-yl-N4,N4'-diphenyl-biphenyl-4,4'-diamine (4,4'-bis[N-(1-naphthyl)-N-phenyl-amino]biphenyl), CBP: 4,4-N,N'-dicarbazole-biphenyl, BCP: 2,9-dimethyl-4,7-diphenyl-1,10-phenanthroline, Ir(ppy)₃: fac tris(2-phenylpyridine)iridium (iridium-phenylpyridine complex), and PtEOP: 2,3,7,8,12,13,17,18-octaethyl-21H,23H-porphine platinum (platinum-octaethyl porphine complex).

The phosphorescence (luminescence) material used in the luminescence layer 12 has attracted notice. This is because the phosphorescence material is expected to provide a higher luminescence efficiency in principle.

More specifically, in the case of the phosphorescence material, excitons produced by a recombination of carriers comprise singlet excitons and triplet excitons presented in a ratio of 1:3. For this reason, when fluorescence caused during the transition from the singlet excited state to the ground state is utilized, a resultant luminescence efficiency is 25% (as upper limit) based on all the produced excitons in principle.

On the other hand, in the case of utilizing phosphorescence caused during a transition from the triplet excited state, a resultant luminescence efficiency is expected to be at least three times that of the case of fluorescence in principle. In addition thereto, if an intersystem crossing from the singlet excited state (higher energy level) to the triplet excited state is taken into consideration, the luminescence efficiency of phosphorescence can be expected to be 100% (four times that of fluorescence) in principle.

The use of phosphorescence based on transition from the triplet excited state has also been proposed in, e.g., Japanese Laid-Open Patent Application (JP-A) 11-329739, JP-A 11-256148 and JP-A 8-319482.

However, the above-mentioned organic EL devices utilizing phosphorescence have a problem associated with luminescent deterioration particularly in an energized state.

The reason for luminescent deterioration has not been clarified as yet but may be attributable to such a phenomenon that the life of triplet exciton is generally longer than that of singlet exciton by at least three digits, so that a molecule is placed in a higher-energy state for a long period, causing a reaction with an ambient substance, formation of exciplex or excimer, a change in a minute molecular structure, a structural change of an ambient substance, etc.

Accordingly, the (electro)phosphorescence EL device is expected to provide a higher luminescence efficiency as described above, while the EL device is required to suppress or minimize the luminescent deterioration in the energized state.

SUMMARY OF THE INVENTION

An object of the present invention is to provide a luminescence device capable of providing a high-efficiency luminescent state at a high brightness (or luminance) for a long period while minimizing the deterioration in luminescence in the energized state.

Another object of the present invention is to provide a metal coordination compound as a material suitable for an organic layer for the luminescence device.

According to the present invention, there is provided a luminescence device, comprising: an organic compound layer comprising a metal coordination compound having a partial structure represented by the following formula (1):

wherein each of N and C represents an atom constituting a cyclic group.

According to the present invention, there is also provided a metal coordination compound, adapted for use in a luminescence device, having a partial structure represented by the following formula (1):

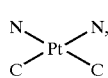

(1)

wherein each of N and C represents an atom constituting a cyclic group.

These and other objects, features and advantages of the present invention will become more apparent upon a consideration of the following description of the preferred embodiments of the present invention taken in conjunction with the accompanying drawing.

DESCRIPTION OF THE PREFERRED EMBODIMENTS

Figure 1A:
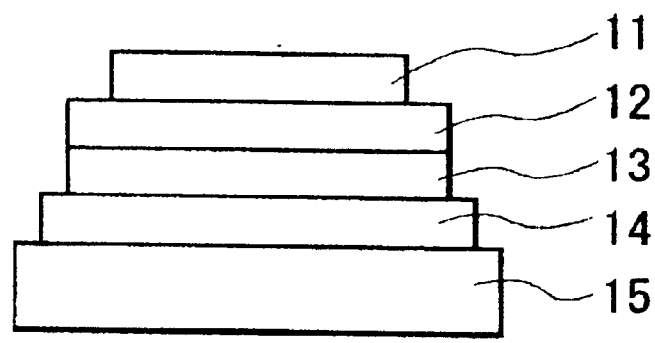
FIGS. 1A, 1B and 1C are respectively a schematic sectional view of a layer structure of a luminescence device.

In the case where a luminescence layer for an organic EL device is formed of a carrier transporting host material and a phosphorescent guest material, a process of emission of light (phosphorescence) may generally involve the following steps:

(1) transport of an electron and a hole within a luminescence layer, (2) formation of an exciton of the host material, (3) transmission of excited energy between host material molecules, (4) transmission of excited energy from the host material molecule to the guest material molecule, (5) formation of a triplet exciton of the guest material, and (6) emission of light (phosphorescence) caused during a transition from the triplet excited state to the ground state of the guest material.

In the above steps, desired energy transmission and luminescence may generally be caused based on various deactivation and competition.

In order to improve a luminescence efficiency of the EL device, a luminescence center material per se is required to provide a higher yield of a luminescence quantum. In addition thereto, an efficient energy transfer between host material molecules and/or between host material molecule and guest material molecule is also an important factor.

Further, the above-described luminescent deterioration in an energized state may presumably relate to the luminescent center material per se or an environmental change thereof by its ambient molecular structure.

For this reason, our research group has extensively investigated an effect of the use of the metal coordination compound (platinum complex) having a partial structure of formula (1) as the luminescent center material, and as a result has found that the metal coordination compound having the partial structure of formula (1) allows a high-efficiency luminescence (e.g., luminescence efficiency of at least 1 cd/W) with a high brightness (luminance) for a long period (e.g., a luminance half-life of at least 500 hours at an initial luminance of 100 cd/m$^2$)(i.e., a decreased luminescent deterioration in an energized state).

The metal coordination compound having a partial structure of formula (1) may preferably be represented by any one of the following formulas (1-1) to (1-6):

(1-1)

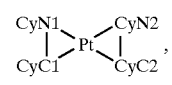

(1-2)

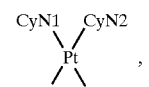

(1-3)

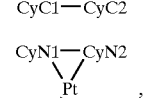

(1-4)

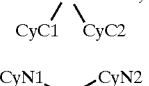

(1-5)

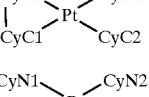

(1-6)

wherein CyN1 and CyN2 independently denote a cyclic group containing a nitrogen atom connected to Pt and capable of having a substituent, and CyC1 and CyC2 independently denote a cyclic group containing a carbon atom connected to Pt and capable of having a substituent, each of the substituents for CyN1, CyN2, CyC1 and CyC2 being selected from the group consisting of a halogen atom; nitro group; a trialkylsilyl group containing three linear or branched alkyl groups each independently having 1–8 carbon atoms; and a linear or branched alkyl group having 1–20 carbon atoms capable of including one or at least two non-neighboring methylene groups which can be replaced with —O—, —S—, —CO—, —CO—O—, —O—CO—, —CH=CH— or —C≡C— and capable of including a hydrogen atom which can be replaced with a fluorine atom.

The metal coordination compound may more preferably be represented by the formula (1-1) or the formula (1-2) in order to allow further improved high-efficient luminance while minimizing the luminescent deterioration in the energized state.

At least one of CyN1 and CyN2 in the formulas (1-1) to (1-6) may preferably be a substituted or unsubstituted cyclic group having a ring structure selected from the group consisting of pyridine, pyrimidine, pyrazoline, pyrrole, pyrazole, quinoline, isoquinoline, and quinoxaline. Further, at least one of CyC1 and CyC2 in the formulas (1-1) to (1-6) may preferably be a substituted or unsubstituted cyclic group selected from the group consisting of phenyl, naphthyl, thienyl, benzothienyl, and quinolyl.

The metal coordination compound (platinum complex) specifically represented by the above formulas (1-1) to (1-6) causes phosphorescence (luminescence) and is assumed to have a lowest excited state comprising a triplet excited state likely to cause a metal-to-ligand charge transfer (MLCT* state). The phosphorescent emission of light (phosphorescence) is produced during the transition from the MLCT* state to the ground state.

The metal coordination compound according to the present invention has been found to provide a higher phosphorescence yield of 0.05–0.9 and a shorter phosphorescence life of 1–30 μsec.

A phosphorescence yield (P(m)) is obtained based on the following equation:

$P(m)/P(s)=(S(m)/S(s))\times(A(s)/A(m))$, wherein P(m) represents a phosphorescence yield of an (unknown) objective luminescent material, P(s) represents a known (standard) phosphorescence yield of a standard luminescent material (Ir(ppy)$_3$), S(m) represents an integrated intensity of (photo-)excited emission spectrum of the objective material, S(s) represents a known integrated intensity of the standard material, A(m) represents an absorption spectrum of an excited light wavelength of the objective material, and A(s) represents a known absorption spectrum of the standard material.

The shorter phosphorescence life is necessary to provide a resultant EL device with a higher luminescence efficiency. This is because the longer phosphorescence life increases molecules placed in their triplet excited state, which is a waiting state for phosphorescence, thus lowering the resultant luminescence efficiency particularly at a higher current density.

Accordingly, the metal coordination compound according to the present invention is a suitable luminescent material for an EL device with a higher phosphorescence yield and a shorter phosphorescence life.

In a conventional phosphorescent EL device, the platinum-porphine complex (e.g., PtOEP described above) is used as the luminescent material. On the other hand, the metal coordination compound according to the present invention has a carbon-platinum bond (C—Pt bond) in its molecular structure, thus particularly effectively exhibiting a heavy atom effect of platinum (Pt) compared to the case of N—Pt bond (in PtOEP). As a result, a spin-orbit interaction is enhanced to realize a higher phosphorescence yield and a shorter phosphorescence life at the same time.

Further, molecules of the metal coordination compound have a shorter time period wherein they stay in the triplet excited state, thus prolonging the life of the EL device with less deterioration. In this regard, the metal coordination compound according to the present invention has been substantiated to exhibit excellent stability of luminance as shown in the Examples hereinafter.

In the case of a phosphorescent (luminescent) material, luminescent characteristics are largely affected by the molecular environment. On the other hand, principal characteristics of the fluorescent material are studied based on photoluminescence.

For this reason, results of photoluminescence of the phosphorescent material do not reflect the luminescent characteristics of the resultant EL device in many cases since the luminescent characteristics in the case of the phosphorescent material depend on a magnitude of the polarity of the ambient host material molecules, the ambient temperature, and the state of the material (e.g., solid state or liquid state, etc.) Accordingly, different from the fluorescent material, it is generally difficult to expect the resultant EL characteristics for the phosphorescent material by simply removing a part of the characteristics from photoluminescence results.

As a feature of the molecular structure, the platinum complex has a planar structure, and the energy transfer of triplet exciton (i.e., energy transfer from the host material molecule in the triplet excited state to the guest material molecule) is performed based on the electron exchange between adjacent molecules (so-called Dexter transfer). Accordingly, a degree of overlapping of the electron clouds between adjacent molecules is an important factor, so that the planar (molecular) structure is suitable for an efficient energy transfer.

On the other hand, Ir(ppy)$_3$ (indium-phenylpyrimidine complex) as used in the above-described conventional EL device has a steric octahedral coordination structure, thus failing to perform an efficient energy transfer (Dexter transfer) from the host material molecule.

As described above, the metal coordination compound (platinum complex) according to the present invention is a suitable luminescent material for an EL device.

The luminescence device (EL) device according to the present invention employs the above-mentioned metal coordination compound in an organic layer, particularly a luminescence layer.

Specifically, the luminescence device may preferably include the organic layer comprising the metal coordination compound between a pair of oppositely disposed electrodes comprising a transparent electrode (anode) and a metal electrode (cathode) which are supplied with a voltage to cause luminescence, thus constituting an electric-field luminescence device.

Figure 1B:
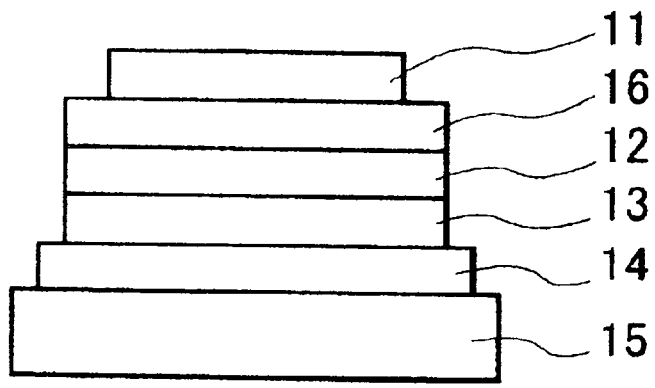
Figure 1C:
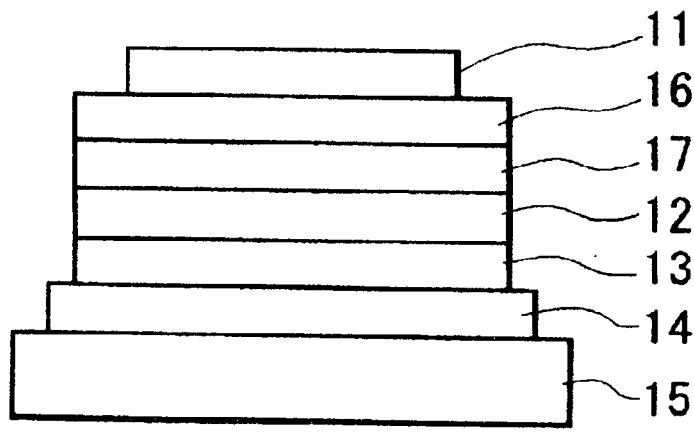

The luminescence device of the present invention has a layer structure shown in FIGS. 1A to 1C as specifically described above.

By the use of the metal coordination compound of the present invention, the resultant luminescence device has a high luminescence efficiency as described above.

The luminescence device according to the present invention may be applicable to devices required to allow energy saving and high luminance, such as those for a display apparatus and an illumination apparatus, a light source for printers, and a backlight (unit) for a liquid crystal display apparatus. Specifically, in the case of using the luminescence device of the present invention in the display apparatus, it is possible to provide a flat panel display apparatus capable of exhibiting an excellent energy saving performance, a high visibility and a good lightweight property. With respect to the light source, it becomes possible to replace a laser light source of a laser beam printer, which is currently used widely, with the luminescence device according to the present invention. Further, when the luminescence device of the present invention is arranged in independently addressable arrays as an exposure means for effecting desired exposure of light to a photosensitive drum for forming an image, it becomes possible to considerably reduce the volume (size) of the image forming apparatus. With respect to the illumination apparatus and the backlight (unit), the resultant apparatus (unit) using the luminescence device of the present invention is expected to have an energy saving effect.

Hereinbelow, the metal coordination compound used in the luminescence device of the present invention will be described more specifically.

Specific and non-exhaustive examples of the metal coordination compound preferably having the above-mentioned formulas (1-1) to (1-6) may include those (Example Compound Nos. 101–267) shown in Tables 1–7.

In Tables 1–7, abbreviations for respective cyclic groups (CyN1, CyN2, CyC1, CyC2) represent groups shown below.

Pr:

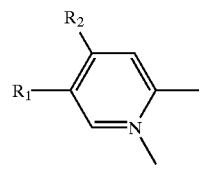

Pd:
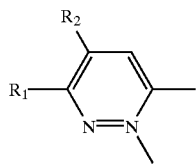
Py1:
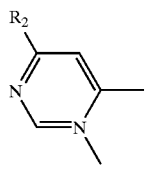
Pa:
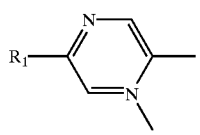
Pa:
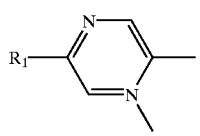
Py2:
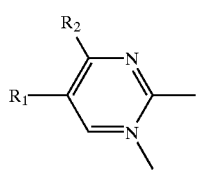
Pz:
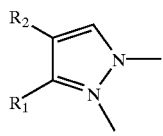
Pr':
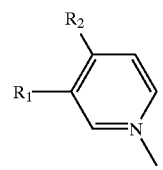
Pd':
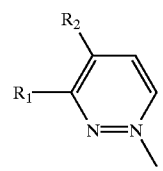
Py1':
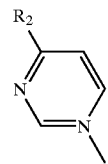
Pa':
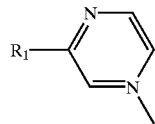
Py2':
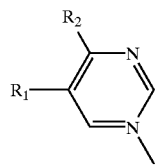
Pz':
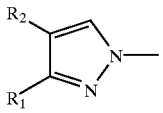
In the above structural formulas, an unconnected covalent (single) linkage extended from nitrogen atom (N) in a lower-right direction except for Pz' is a linkage connected to the platinum atom (Pt), and the other unconnected covalent linkage is a linkage connected to an adjacent cyclic group.
Ph:
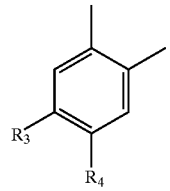
Tn1:
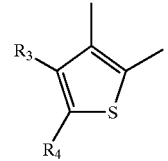
Tn2:
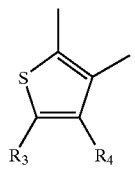

-continued
BTn1:
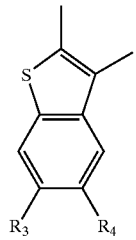
BTn2:
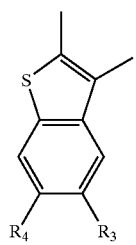
Np:
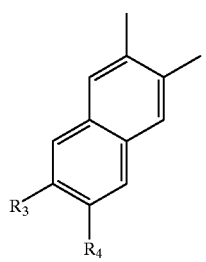
Qn1:
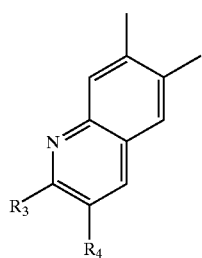
Qn2:
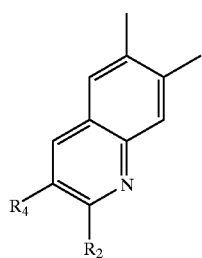
-continued
Qx:
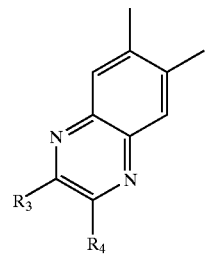
Qz1:
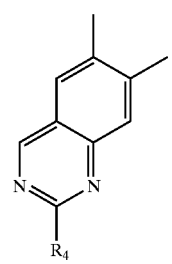
Qz2:
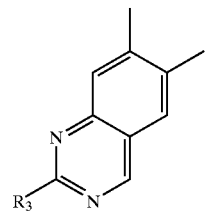
Cn1:
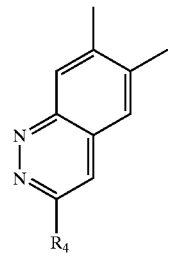
Cn2:
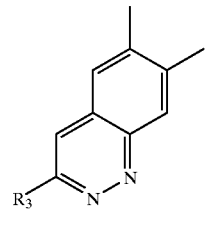
Pz:
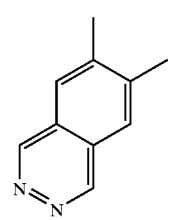

-continued
Ph′: 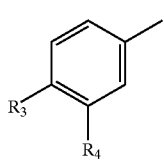
Tn1′: 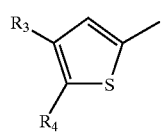
Tn2′: 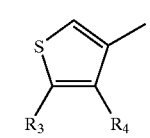
BTn1′: 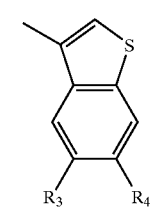
BTn2′: 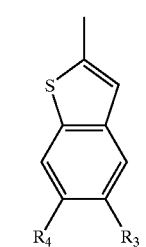
Np′: 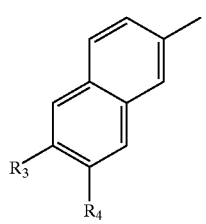
Qn1′: 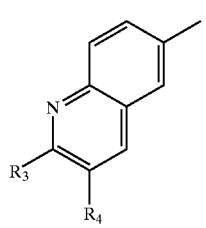
-continued
Qn2′: 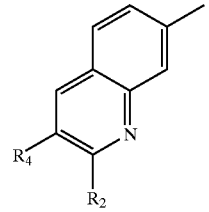
Qx′: 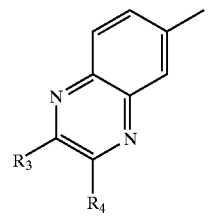
Qz1′: 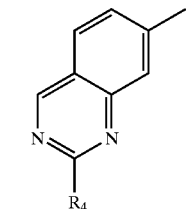
Qz2′: 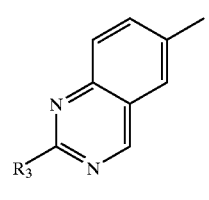
Cn1′: 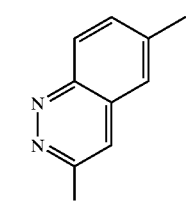
Cn2′: 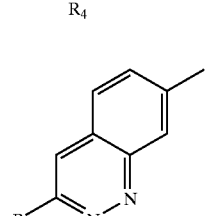
Pz′: 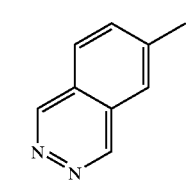
In the above structural formulas (Ph to Pz and Ph′ to Pz′), an unconnected covalent (single) linkage extended in an upper-right direction is a linkage connected to the platinum atom (Pt), and the other unconnected covalent linkage extended in an upper direction is a linkage connected to an adjacent cyclic group.

TABLE 1

| Ex. Comp. | Formula | CyN1 | CyN2 | CyC1 | CyC2 | R1 | R2 | R3 | R4 |
|---|---|---|---|---|---|---|---|---|---|
| 101 | (1-1) | Pr | Pr | Ph | Ph | H | H | H | H |
| 102 | (1-1) | Pr | Pr | Tn1 | Tn1 | H | H | H | H |
| 103 | (1-1) | Pr | Pr | Tn2 | Tn2 | H | H | H | H |
| 104 | (1-1) | Pr | Pr | Tn3 | Tn3 | H | H | H | H |
| 105 | (1-1) | Pr | Pr | BTn1 | BTn1 | H | H | H | H |
| 106 | (1-1) | Pr | Pr | BTn2 | BTn2 | H | H | H | H |
| 107 | (1-1) | Pr | Pr | Np | Np | H | H | H | H |
| 108 | (1-1) | Pr | Pr | Qn1 | Qn1 | H | H | H | H |
| 109 | (1-1) | Pr | Pr | Qn2 | Qn2 | H | H | H | H |
| 110 | (1-1) | Pa | Pa | Ph | Ph | H | H | H | H |
| 111 | (1-1) | Pa | Pa | Tn1 | Tn1 | H | H | H | H |
| 112 | (1-1) | Pa | Pa | Tn2 | Tn2 | H | H | H | H |
| 113 | (1-1) | Pa | Pa | Tn3 | Tn3 | H | H | H | H |
| 114 | (1-1) | Pa | Pa | BTn1 | BTn1 | H | H | H | H |
| 115 | (1-1) | Pa | Pa | BTn2 | BTn2 | H | H | H | H |
| 116 | (1-1) | Pa | Pa | Np | Np | H | H | H | H |
| 117 | (1-1) | Pa | Pa | Qn1 | Qn1 | H | H | H | H |
| 118 | (1-1) | Pa | Pa | Qn2 | Qn2 | H | H | H | H |
| 119 | (1-1) | Pz | Pz | Ph | Ph | H | H | H | H |
| 120 | (1-1) | Pz | Pz | Tn1 | Tn1 | H | H | H | H |
| 121 | (1-1) | Pz | Pz | Tn2 | Tn2 | H | H | H | H |
| 122 | (1-1) | Pz | Pz | Tn3 | Tn3 | H | H | H | H |
| 123 | (1-1) | Pz | Pz | BTn1 | BTn1 | H | H | H | H |
| 124 | (1-1) | Pz | Pz | BTn2 | BTn2 | H | H | H | H |
| 125 | (1-1) | Pz | Pz | Np | Np | H | H | H | H |

TABLE 2

| Ex. Comp. | Formula | CyN1 | CyN2 | CyC1 | CyC2 | R1 | R2 | R3 | R4 |
|---|---|---|---|---|---|---|---|---|---|
| 126 | (1-1) | Pz | Pz | Qn1 | Qn1 | H | H | H | H |
| 127 | (1-1) | Pz | Pz | Qn2 | Qn2 | H | H | H | H |
| 128 | (1-2) | Pr | Pr | Ph | Ph | H | H | H | H |
| 129 | (1-2) | Pr | Pr | Tn1 | Tn1 | H | H | H | H |
| 130 | (1-2) | Pr | Pr | Tn2 | Tn2 | H | H | H | H |
| 131 | (1-2) | Pr | Pr | BTn1 | BTn1 | H | H | H | H |
| 132 | (1-2) | Pr | Pr | BTn2 | BTn2 | H | H | H | H |
| 133 | (1-2) | Pr | Pr | Np | Np | H | H | H | H |
| 134 | (1-2) | Pr | Pr | Qn1 | Qn1 | H | H | H | H |
| 135 | (1-2) | Pr | Pr | Qn2 | Qn2 | H | H | H | H |
| 136 | (1-2) | Pr | Pr | Qx | Qx | H | H | H | H |
| 137 | (1-2) | Pr | Pr | Qz1 | Qz1 | H | H | H | H |
| 138 | (1-2) | Pr | Pr | Qz2 | Qz2 | H | H | H | H |
| 139 | (1-2) | Pr | Pr | Cn1 | Cn1 | H | H | H | H |
| 140 | (1-2) | Pr | Pr | Cn2 | Cn2 | H | H | H | H |
| 141 | (1-2) | Pr | Pr | Pz | Pz | H | H | H | H |
| 142 | (1-2) | Pd | Pd | Ph | Ph | H | H | H | H |
| 143 | (1-2) | Pd | Pd | Tn1 | Tn1 | H | H | H | H |
| 144 | (1-2) | Pd | Pd | Tn2 | Tn2 | H | H | H | H |
| 145 | (1-2) | Pd | Pd | BTn1 | BTn1 | H | H | H | H |
| 146 | (1-2) | Pd | Pd | BTn2 | BTn2 | H | H | H | H |
| 147 | (1-2) | Pd | Pd | Np | Np | H | H | H | H |
| 148 | (1-2) | Pd | Pd | Qn1 | Qn1 | H | H | H | H |
| 149 | (1-2) | Pd | Pd | Qn2 | Qn2 | H | H | H | H |
| 150 | (1-2) | Pd | Pd | Qx | Qx | H | H | H | H |

TABLE 3

| Ex. Comp. | Formula | CyN1 | CyN2 | CyC1 | CyC2 | R1 | R2 | R3 | R4 |
|---|---|---|---|---|---|---|---|---|---|
| 151 | (1-2) | Pd | Pd | Qz1 | Qz1 | H | H | H | H |
| 152 | (1-2) | Pd | Pd | Qz2 | Qz2 | H | H | H | H |
| 153 | (1-2) | Pd | Pd | Cn1 | Cn1 | H | H | H | H |
| 154 | (1-2) | Pd | Pd | Cn2 | Cn2 | H | H | H | H |
| 155 | (1-2) | Pd | Pd | Pz | Pz | H | H | H | H |
| 156 | (1-2) | Py1 | Py1 | Ph | Ph | H | H | H | H |
| 157 | (1-2) | Py1 | Py1 | Tn1 | Tn1 | H | H | H | H |
| 158 | (1-2) | Py1 | Py1 | Tn2 | Tn2 | H | H | H | H |
| 159 | (1-2) | Py1 | Py1 | BTn1 | BTn1 | H | H | H | H |
| 160 | (1-2) | Py1 | Py1 | BTn2 | BTn2 | H | H | H | H |
| 161 | (1-2) | Py1 | Py1 | Np | Np | H | H | H | H |
| 162 | (1-2) | Py1 | Py1 | Qn1 | Qn1 | H | H | H | H |
| 163 | (1-2) | Py1 | Py1 | Qn2 | Qn2 | H | H | H | H |
| 164 | (1-2) | Py1 | Py1 | Qx | Qx | H | H | H | H |
| 165 | (1-2) | Py1 | Py1 | Qz1 | Qz1 | H | H | H | H |
| 166 | (1-2) | Py1 | Py1 | Qz2 | Qz2 | H | H | H | H |
| 167 | (1-2) | Py1 | Py1 | Cn1 | Cn1 | H | H | H | H |
| 168 | (1-2) | Py1 | Py1 | Cn2 | Cn2 | H | H | H | H |
| 169 | (1-2) | Py1 | Py1 | Pz | Pz | H | H | H | H |
| 170 | (1-2) | Pa | Pa | Ph | Ph | H | H | H | H |
| 171 | (1-2) | Pa | Pa | Tn1 | Tn1 | H | H | H | H |
| 172 | (1-2) | Pa | Pa | Tn2 | Tn2 | H | H | H | H |
| 173 | (1-2) | Pa | Pa | BTn1 | BTn1 | H | H | H | H |
| 174 | (1-2) | Pa | Pa | BTn2 | BTn2 | H | H | H | H |
| 175 | (1-2) | Pa | Pa | Np | Np | H | H | H | H |

TABLE 4

| Ex. Comp. | Formula | CyN1 | CyN2 | CyC1 | CyC2 | R1 | R2 | R3 | R4 |
|---|---|---|---|---|---|---|---|---|---|
| 176 | (1-2) | Pa | Pa | Qn1 | Qn1 | H | H | H | H |
| 177 | (1-2) | Pa | Pa | Qn2 | Qn2 | H | H | H | H |
| 178 | (1-2) | Pa | Pa | Qx | Qx | H | H | H | H |
| 179 | (1-2) | Pa | Pa | Qz1 | Qz1 | H | H | H | H |
| 180 | (1-2) | Pa | Pa | Qz2 | Qz2 | H | H | H | H |
| 181 | (1-2) | Pa | Pa | Cn1 | Cn1 | H | H | H | H |
| 182 | (1-2) | Pa | Pa | Cn2 | Cn2 | H | H | H | H |
| 183 | (1-2) | Pa | Pa | Pz | Pz | H | H | H | H |
| 184 | (1-2) | Py2 | Py2 | Ph | Ph | H | H | H | H |
| 185 | (1-2) | Py2 | Py2 | Tn1 | Tn1 | H | H | H | H |
| 186 | (1-2) | Py2 | Py2 | Tn2 | Tn2 | H | H | H | H |
| 187 | (1-2) | Py2 | Py2 | BTn1 | BTn1 | H | H | H | H |
| 188 | (1-2) | Py2 | Py2 | BTn2 | BTn2 | H | H | H | H |
| 189 | (1-2) | Py2 | Py2 | Np | Np | H | H | H | H |
| 190 | (1-2) | Py2 | Py2 | Qn1 | Qn1 | H | H | H | H |
| 191 | (1-2) | Py2 | Py2 | Qn2 | Qn2 | H | H | H | H |
| 192 | (1-2) | Py2 | Py2 | Qx | Qx | H | H | H | H |
| 193 | (1-2) | Py2 | Py2 | Qz1 | Qz1 | H | H | H | H |
| 194 | (1-2) | Py2 | Py2 | Qz2 | Qz2 | H | H | H | H |
| 195 | (1-2) | Py2 | Py2 | Cn1 | Cn1 | H | H | H | H |
| 196 | (1-2) | Py2 | Py2 | Cn2 | Cn2 | H | H | H | H |
| 197 | (1-2) | Py2 | Py2 | Pz | Pz | H | H | H | H |
| 198 | (1-2) | Pz | Pz | Ph | Ph | H | H | H | H |
| 199 | (1-2) | Pz | Pz | Tn1 | Tn1 | H | H | H | H |
| 200 | (1-2) | Pz | Pz | Tn2 | Tn2 | H | H | H | H |

TABLE 5

| Ex. Comp. | Formula | CyN1 | CyN2 | CyC1 | CyC2 | R1 | R2 | R3 | R4 |
|---|---|---|---|---|---|---|---|---|---|
| 201 | (1-2) | Pz | Pz | BTn1 | BTn1 | H | H | H | H |
| 202 | (1-2) | Pz | Pz | BTn2 | BTn2 | H | H | H | H |
| 203 | (1-2) | Pz | Pz | Np | Np | H | H | H | H |
| 204 | (1-2) | Pz | Pz | Qn1 | Qn1 | H | H | H | H |
| 205 | (1-2) | Pz | Pz | Qn2 | Qn2 | H | H | H | H |
| 206 | (1-2) | Pz | Pz | Qx | Qx | H | H | H | H |
| 207 | (1-2) | Pz | Pz | Qz1 | Qz1 | H | H | H | H |
| 208 | (1-2) | Pz | Pz | Qz2 | Qz2 | H | H | H | H |
| 209 | (1-2) | Pz | Pz | Cn1 | Cn1 | H | H | H | H |
| 210 | (1-2) | Pz | Pz | Cn2 | Cn2 | H | H | H | H |
| 211 | (1-2) | Pz | Pz | Pz | Pz | H | H | H | H |

TABLE 5-continued

| Ex. Comp. | Formula | CyN1 | CyN2 | CyC1 | CyC2 | R1 | R2 | R3 | R4 |
|---|---|---|---|---|---|---|---|---|---|
| 212 | (1-3) | Pr' | Pr' | Ph | Ph | H | H | H | H |
| 213 | (1-3) | Pd' | Pd' | Ph | Ph | H | H | H | H |
| 214 | (1-3) | Py1' | Py1' | Ph | Ph | H | H | H | H |
| 215 | (1-3) | Pa' | Pa' | Tn1 | Tn1 | H | H | H | H |
| 216 | (1-3) | Py2' | Py2' | Tn2 | Tn2 | H | H | H | H |
| 217 | (1-3) | Pz2' | Pz2' | BTn1 | BTn1 | H | H | H | H |
| 218 | (1-4) | Pr | Pr | Ph' | Ph' | H | H | H | H |
| 219 | (1-4) | Pd | Pd | Ph' | Ph' | H | H | H | H |
| 220 | (1-4) | Py1 | Py1 | Tn1' | Tn1' | H | H | H | H |
| 221 | (1-4) | Pa | Pa | Tn1' | Tn1' | H | H | H | H |
| 222 | (1-4) | Py2 | Py2 | Qx' | Qx' | H | H | H | H |
| 223 | (1-4) | Pz2 | Pz2 | Qz1' | Qz1' | H | H | H | H |
| 224 | (1-5) | Pr | Pr' | Ph | Ph' | H | H | H | H |
| 225 | (1-5) | Pd | Pr' | Ph | Ph' | H | H | H | H |

Of the metal coordination compound preferably having the above-mentioned formulas (1-1) to (1-6), those of formulas (1-1) and (1-2) may, e.g., be synthesized through the following reaction schemes.

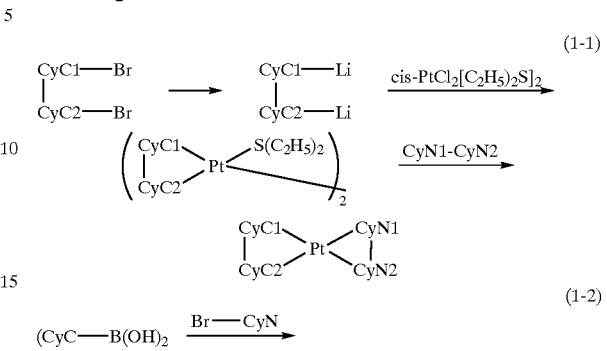

(1-1)

(1-2)

TABLE 6

| Ex. Comp. | Formula | CyN1 | CyN2 | CyC1 | CyC2 | R1 | R2 | R3 | R4 |
|---|---|---|---|---|---|---|---|---|---|
| 226 | (1-5) | Pr | Pr' | Tn1 | Ph' | H | H | H | H |
| 227 | (1-5) | Pa | Pr' | Ph | Ph' | H | H | H | H |
| 228 | (1-5) | Pz | Pr' | Tn1 | Ph' | H | H | H | H |
| 229 | (1-5) | Pz | Pr' | Tn2 | Ph' | H | H | H | H |
| 230 | (1-6) | Pr' | Pr' | Ph' | Ph' | H | H | H | H |
| 231 | (1-6) | Pa' | Pa' | Ph' | Ph' | H | H | H | H |
| 232 | (1-6) | Pz' | Pz' | Ph' | Ph' | H | H | H | H |
| 233 | (1-2) | Pr | Pr | Ph | Ph | H | $OCH_3$ | H | H |
| 234 | (1-2) | Pr | Pr | Ph | Ph | $CF_3$ | H | H | H |
| 235 | (1-2) | Pr | Pr | Ph | Ph | H | $OCF_3$ | H | H |
| 236 | (1-2) | Pr | Pr | Ph | Ph | H | F | H | H |
| 237 | (1-2) | Pr | Pr | Ph | Ph | F | H | H | H |
| 238 | (1-2) | Pr | Pr | Ph | Ph | H | $C_2H_5$ | H | H |
| 239 | (1-2) | Pr | Pr | Ph | Ph | $C_2H_5$ | H | H | H |
| 240 | (1-2) | Pr | Pr | Ph | Ph | H | H | H | $CH_3$ |
| 241 | (1-2) | Pr | Pr | Ph | Ph | H | H | H | $C_3H_7$ |
| 242 | (1-2) | Pr | Pr | Ph | Ph | H | H | H | $OCH_3$ |
| 243 | (1-2) | Pr | Pr | Ph | Ph | H | H | H | F |
| 244 | (1-2) | Pr | Pr | Ph | Ph | H | H | H | $NO_2$ |
| 245 | (1-2) | Pr | Pr | Ph | Ph | H | H | $NO_2$ | H |
| 246 | (1-2) | Pr | Pr | Ph | Ph | H | H | H | $CH_3CH\equiv CHCH_2CH_3$ |
| 247 | (1-2) | Pr | Pr | Ph | Ph | H | H | H | $CH_3C=CH_2CH_3$ |
| 248 | (1-2) | Pr | Pr | Ph | Ph | H | H | H | $CF_3$ |
| 249 | (1-2) | Pr | Pr | Ph | Ph | H | H | U | $COOC_2H_5$ |
| 250 | (1-2) | Pr | Pr | Ph | Ph | H | H | U | $COOC_3H_7$ |

TABLE 7

| Ex. Comp. | Formula | CyN1 | CyN2 | CyC1 | CyC2 | R1 | R2 | R3 | R4 |
|---|---|---|---|---|---|---|---|---|---|
| 251 | (1-2) | Pr | Pr | Ph | Ph | H | H | $CH_3$ | H |
| 252 | (1-2) | Pr | Pr | Ph | Ph | H | H | F | H |
| 253 | (1-2) | Pr | Pr | Ph | Ph | H | H | $OCH_3$ | H |
| 254 | (1-2) | Pr | Pr | Ph | Ph | H | H | H | $SCH_3$ |
| 255 | (1-2) | Pr | Pr | Tn1 | Tn1 | H | H | H | $Si(CH_3)_3$ |
| 256 | (1-2) | Pr | Pr | Tn1 | Tn1 | H | H | H | $CH_3$ |
| 257 | (1-2) | Pr | Pr | Tn1 | Tn1 | H | H | H | $OCH_3$ |
| 258 | (1-2) | Pr | Pr | Tn1 | Tn1 | H | H | H | F |
| 259 | (1-2) | Pr | Pr | Tn1 | Tn1 | H | H | H | $CF_3$ |
| 260 | (1-2) | Pr | Pr | Tn1 | Tn1 | H | H | H | $C_3H_7$ |
| 261 | (1-2) | Pr | Pr | Tn1 | Tn1 | F | H | H | H |
| 262 | (1-2) | Pr | Pr | Tn1 | Tn1 | H | $CH_3$ | H | H |
| 263 | (1-2) | Pr | Pr | Tn1 | Tn1 | H | $OCH_3$ | H | H |
| 264 | (1-2) | Pr | Pr | Tn1 | Tn1 | H | $CF_3$ | H | H |
| 265 | (1-4) | Pr | Pr | Ph' | Ph' | H | H | $OCH_3$ | $OCH_3$ |
| 266 | (1-6) | Pr' | Pr' | Ph' | Ph' | H | H | $OCH_3$ | H |
| 267 | (1-6) | Pa' | Pa' | Ph' | Ph' | H | H | $OCH_3$ | H |

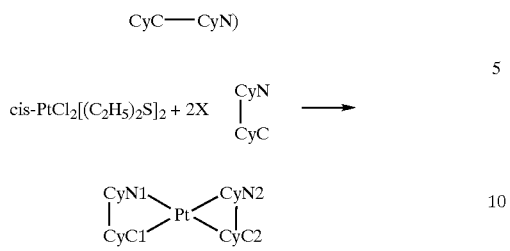
Hereinbelow, the present invention will be described more specifically based on Examples with reference to the drawing.
EXAMPLES 1–11
In these examples, the following metal coordination compounds (Pt complexes) 1–11 were used in respective luminescence layers for Examples 1–11, respectively.
Compound 1
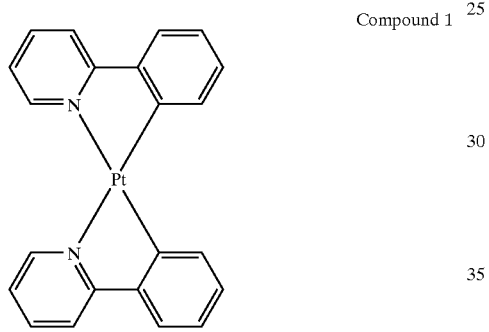
Compound 2
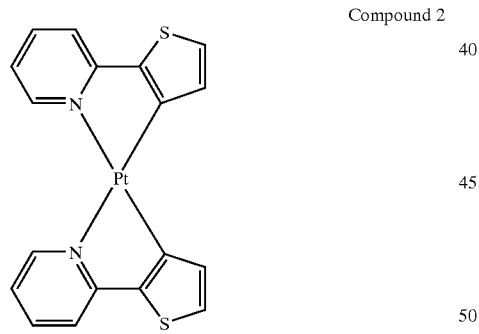
Compound 3
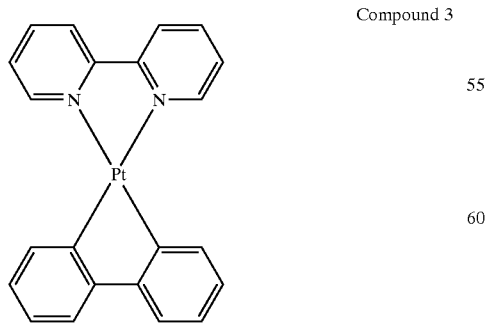
Compound 4
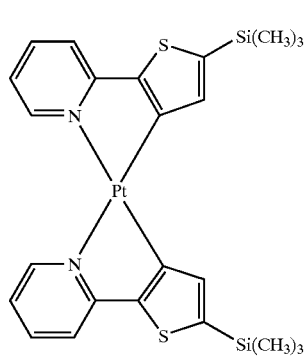
Compound 5
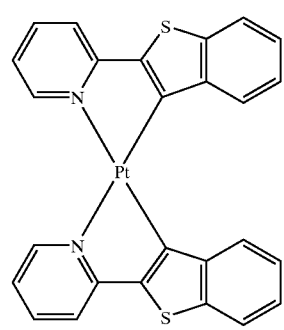
Compound 6
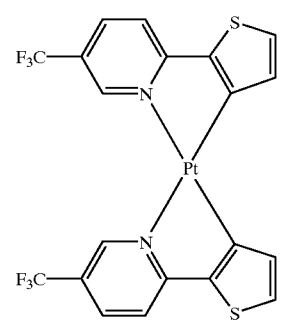
Compound 7
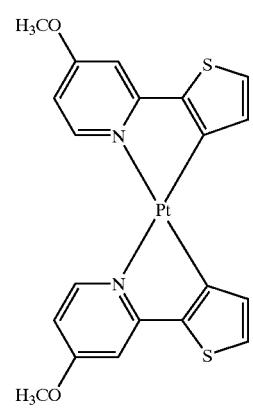

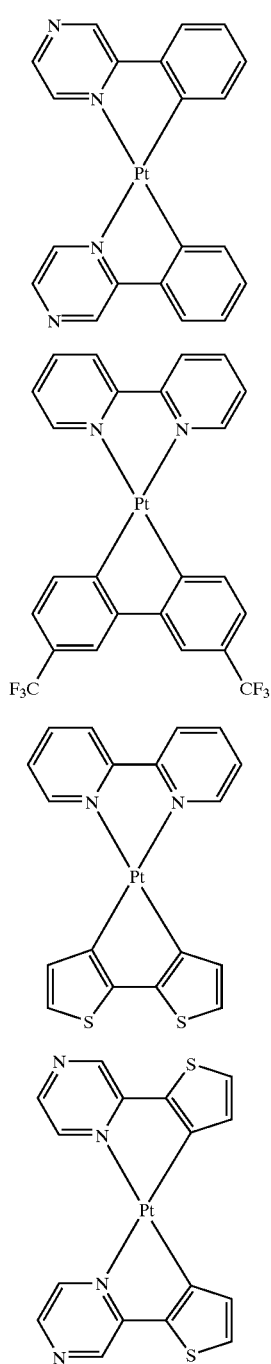

Compound 8

Compound 9

Compound 10

Compound 11

Each of the luminescence devices having a structure shown in FIG. 1B was prepared in the following manner.

On a glass substrate (transparent substrate 15), a 100 nm-thick film (transparent electrode 14) of ITO (indium tin oxide) was formed by sputtering, followed by patterning to have an (opposing) electrode area of 3 mm².

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD

Organic layer 2 (luminescence layer 12) (20 nm): mixture of CBP:Pt complex (metal coordination compound) (95:5 by weight)

Organic layer 3 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

Each of the thus-prepared luminescence devices was taken out of the vacuum chamber and was subjected to a continuous energization test in an atmosphere of a dry nitrogen gas stream so as to remove device deterioration factors, such as oxygen and moisture (water content).

The continuous energization test was performed by continuously applying a voltage at a constant current density of 70 mA/cm² to the luminescence device having the ITO (transparent) electrode (as an anode) and the Al (metal) electrode (as a cathode), followed by a measurement of luminance (brightness) with time so as to determine a time (luminance half-life) required for decreasing an initial luminance (80–120 cd/m²) to ½ thereof.

The results are shown in Table 8 appearing hereinafter.

COMPARATIVE EXAMPLE 1

A comparative luminescence device was prepared and evaluated in the same manner as in Example 1–11 except that the Pt complex (metal coordination compounds 1–11) was changed to Ir-phenylpyrimidine complex (Ir(ppy)₃) shown below.

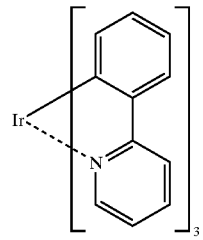

The results are shown in Table 8 below.

TABLE 8

| Ex. No. | Compound No. | Luminance half-life (Hr) |
| --- | --- | --- |
| Ex. 1 | 1 | 500 |
| Ex. 2 | 2 | 400 |
| Ex. 3 | 3 | 600 |
| Ex. 4 | 4 | 650 |
| Ex. 5 | 5 | 950 |
| Ex. 6 | 6 | 800 |
| Ex. 7 | 7 | 850 |
| Ex. 8 | 8 | 600 |
| Ex. 9 | 9 | 450 |
| Ex. 10 | 10 | 900 |
| Ex. 11 | 11 | 550 |
| Comp. Ex. 1 | Ir(ppy)₃ | 350 |

The luminescence devices using the metal coordination compounds 3, 5, 6, 7 and 11 caused red luminescence, and the luminescence devices using the metal coordination compounds 2 and 4 caused orange luminescence. Further, the luminescence devices using the metal coordination compounds 1 and Ir(ppy)₃ caused green luminescence.

EXAMPLE 12 (SYNTHESIS OF COMPOUND 2)

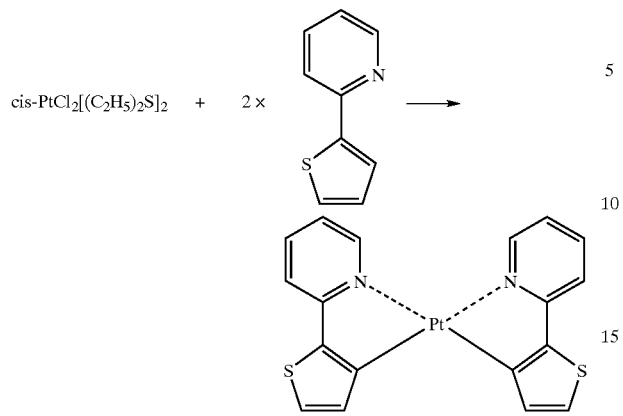

In a 3 liter-three necked flask, 14.6 g (90.6 mM) of 2-(2-thienyl)pyridine and 912 ml of anhydrous ether were placed and stirred at −70° C. or below in an argon gas stream. To the mixture, 62.2 ml (99.5 mM) of 1.6M-t-butyllithium solution in pentane was added dropwise in ca. 35 min., followed by stirring at −70° C. for 40 min. At that temperature, a suspension of 8.5 g (19.0 mM) of cis-PtCl$_2$[(C$_2$H$_5$)$_2$S]$_2$ in a mixture solvent of 289 ml of anhydrous ether and 73 ml of tetrahydrofuran (THF) was added dropwise in ca. 1 hour to the resultant mixture, followed by stirring at −70° C. for 30 min. and a gradual temperature rise up to 0° C. in ca. 2 hours. To the reaction mixture, 912 ml of water was gradually added dropwise at 0° C. The organic layer was washed with common salt aqueous solution and the aqueous (water) layer was subjected to extraction with methylene chloride. The resultant organic layer (from the organic and aqueous layers) was dried with anhydrous sodium sulfate, followed by distilling off the solvent to obtain a residue. The residue was recrystallized from a mixture solvent (hexane/methylene chloride) to obtain 4.50 g of cis-bis[2-(2-thienyl)pyridinato-N,C$^{5'}$] platinum (II) (Yield: 45.8%).

EXAMPLE 13 (SYNTHESIS OF COMPOUND 5)

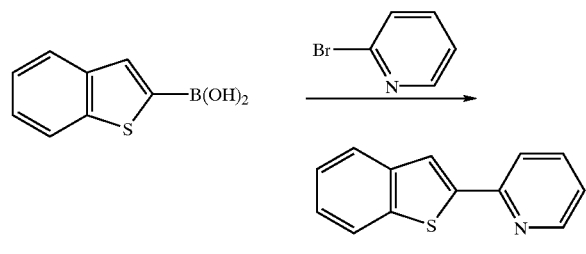

In a 1 liter-three necked flask, 26.6 g (168.5 mM) of 2-bromopyridine, 30.0 g (168.5 mM) of benzo[b]thiophene-2-boronic acid, 170 ml of toluene, 85 ml of ethanol and 170 ml of 2M-sodium carbonate aqueous solution were placed and stirred in a nitrogen gas stream at room temperature. Under stirring, to the mixture, 6.18 g (5.35 mM) of tetrakis (triphenyl-phosphine) palladium (0) was added, followed by heat-refluxing for 5.5 hours under stirring in a nitrogen gas stream.

After the reaction, the reaction mixture was cooled, followed by extraction with cool water and toluene. The organic layer was washed with water until the system showed neutral, followed by distilling off the solvent under reduced pressure to obtain a residue. The residue was purified by silica gel column chromatography (eluent: toluene/hexane=5/1) to obtain a colorless crystal. The crystal was purified by alumina column chromatography (eluent: toluene) and recrystallized from ethanol to obtain 12.6 g of 2-(pyridine-2-yl)benzo[b]thiophene (Yield: 35.4%).

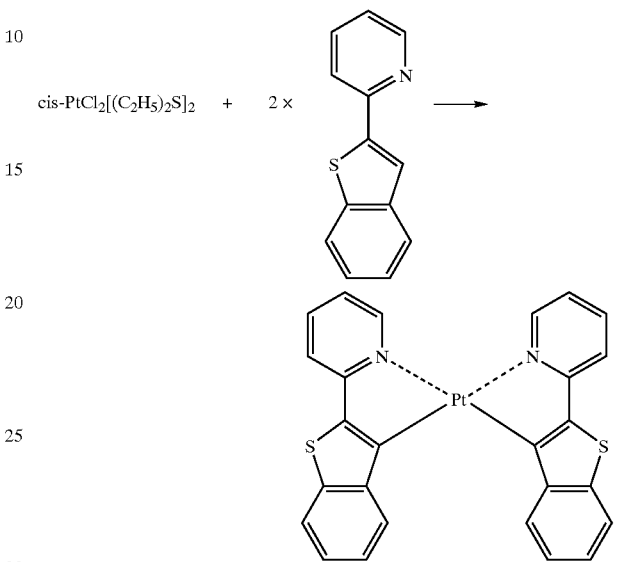

In a 3 liter-three necked flask, 6.73 g (31.9 mM) of 2-(benzo[b]thiophene-2-yl)pyridine and 636 ml of anhydrous ether were placed and stirred at −70° C. or below in an argon gas stream. To the mixture, 21.9 ml (35.0 mM) of 1.6M-t-butyllithium solution in pentane was added dropwise in ca. 20 min., followed by stirring at −70° C. for 50 min. At that temperature, a suspension of 2.97 g (6.68 mM) of cis-PtCl$_2$[(C$_2$H$_5$)$_2$S]$_2$ in a mixture solvent of 101 ml of anhydrous ether and 25 ml of tetrahydrofuran (THE) was added dropwise in ca. 30 min. to the resultant mixture, followed by stirring at −70° C. for 1 hour and a gradual temperature rise up to 0° C. in ca. 2 hours. To the reaction mixture, 318 ml of water was gradually added dropwise at 0° C. The organic layer was washed with a common salt aqueous solution and the aqueous (water) layer was subjected to extraction with methylene chloride. The resultant organic layer (from the organic and aqueous layers) was dried with anhydrous sodium sulfate, followed by distilling off the solvent to obtain a residue. The residue was recrystallized from a mixture solvent (hexane/methylene chloride) to obtain 3.10 g of cis-bis[2-(benzo[b]thiophene-2-yl) pyridinato-N,C$^{5'}$] platinum (II) (Yield: 75.4%).

EXAMPLE 14 (SYNTHESIS OF COMPOUND 3)

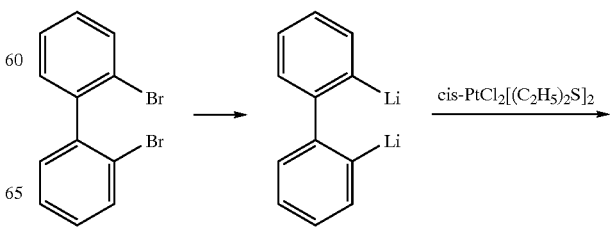

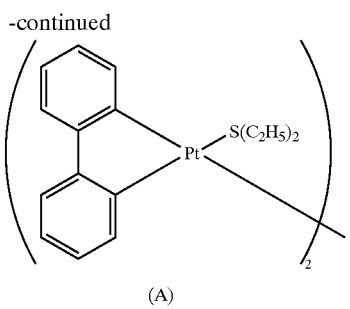

(A)

In a 3 liter-three necked flask, 35.0 g (112 mM) of 2,2'-dibromobiphenyl and 650 ml of anhydrous ether were placed and stirred at −60° C. or below in an argon gas stream. To the mixture, 153 ml (0.245 mM) of 1.6M-n-butyllithium solution in pentane was added dropwise in ca. 50 min., followed by a temperature rise and stirring at room temperature for 3 hours. To a suspension of 25.0 g (56.0 mM) of cis-$PtCl_2[(C_2H_5)_2S]_2$ in 833 ml of anhydrous ether cooled and kept at ±10° C. or below, the resultant mixture was added dropwise in ca. 10 min., followed by stirring at −10° C. for 1 hour and a gradual temperature rise up to 0° C. To the reaction mixture, 417 ml of water was gradually added dropwise at 0° C. The organic layer was washed with a common salt aqueous solution and the aqueous (water) layer was subjected to extraction with methylene chloride. The resultant organic layer (from the organic and aqueous layers) was dried with anhydrous sodium sulfate, followed by distilling off the solvent to obtain a residue. The residue was successively recrystallized from a mixture solvent (hexane/ether) and a mixture solvent (hexane/methylene chloride) to obtain 1.77 g of a compound (A) (Yield: 7.2%).

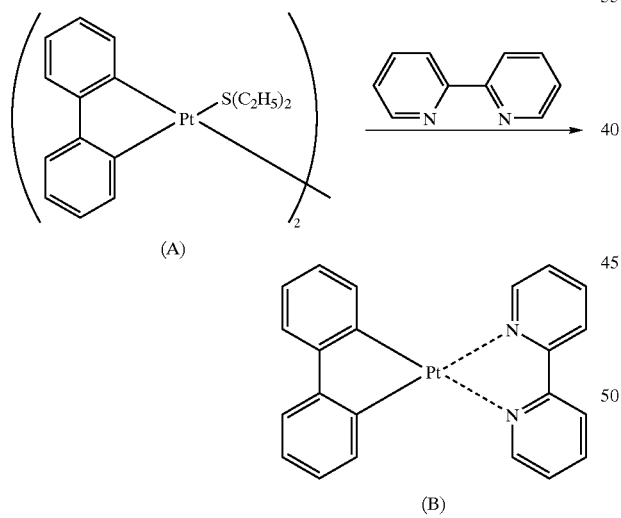

In a 100 ml-three-necked flask, 21.3 g (136 mM) of 2,2'-dipyridyl was placed and melted at 80° C. in an argon gas stream, followed by the addition of 1.73 g (1.98 mM) of the above-prepared compound (A). The mixture was stirred at 80° C. for 10 min. under reduced pressure and cooled to ca. 10° C. to crystallize the mixture. The crystallized mixture was dissolved in methylene chloride, and hexane was added thereto to reprecipitate a crystal. The crystal was recovered by filtration, followed by recrystallization from a mixture solvent (hexane/methylene chloride) to obtain 1.90 g of an objective compound (B) (Yield: 95.4%).

EXAMPLES 15–20 (SYNTHESIS OF COMPOUNDS 1, 4, 6, 7, 8 AND 11)

Compounds 1, 4, 6, 7, 8 and 11 were prepared in a similar manner as in Example 12, respectively.

EXAMPLES 21 AND 22 (SYNTHESIS OF COMPOUNDS 9 AND 10)

Compounds 9 and 10 were prepared in a similar manner as in Example 14, respectively.

As described hereinabove, according to the present invention, the metal coordination compound (Pt complex) preferably having the formulas (1-1) to (1-6) according to the present invention has a higher phosphorescence luminescence efficiency and a shorter phosphorescence life, thus being suitable as a luminescence material for an EL device.

The luminescence device (EL device) using the metal coordination compound according to the present invention allows a high-efficiency luminescence at a high luminescence for a long period of time while minimizing luminescence deterioration in an energized state.

What is claimed is:

1. A luminescence device comprising a pair of electrodes, a luminescence layer disposed between the electrodes and an organic layer, which is disposed between the electrodes and is different from the luminescent layer, the luminescent layer comprising a metal coordination compound represented by formula (4):

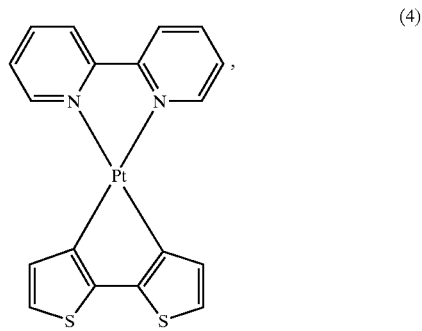

wherein:
(i) the compound of formula (4) is optionally and independently substituted with at least one $C_1$–$C_{20}$ alkyl group, $C_1$–$C_{20}$ alkoxy group or a trimethylsilyl group, which said alkyl, alkoxy and trimethylsilyl groups are optionally substituted with a fluorine; and
(ii) one —CH= in one or both pyridine rings in the compound of formula (4) is optionally replaced with —N=.

* * * * *

UNITED STATES PATENT AND TRADEMARK OFFICE
CERTIFICATE OF CORRECTION

PATENT NO. : 6,780,528 B2 Page 1 of 1
DATED : August 24, 2004
INVENTOR(S) : Akira Tsuboyama et al.

It is certified that error appears in the above-identified patent and that said Letters Patent is hereby corrected as shown below:

Column 6,
Line 39, "—C=C—" should read -- —C≡C— --.

Column 17,
Table 6, "U / U" should read -- H / H --.

Signed and Sealed this

Twenty-first Day of December, 2004

JON W. DUDAS
*Director of the United States Patent and Trademark Office*